(12) United States Patent
Stinson (10) Patent No.: US 7,641,983 B2
(45) Date of Patent: Jan. 5, 2010

(54) MEDICAL DEVICES INCLUDING COMPOSITES

(75) Inventor: Jonathan S. Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 659 days.

(21) Appl. No.: 11/098,201

(22) Filed: Apr. 4, 2005

(65) Prior Publication Data

US 2006/0222844 A1    Oct. 5, 2006

(51) Int. Cl.
*A61F 2/02* (2006.01)
*B22F 1/02* (2006.01)

(52) U.S. Cl. .................. 428/546; 428/323; 428/328; 428/403; 428/570; 623/1.32; 623/1.34

(58) Field of Classification Search ................ None
See application file for complete search history.

(56) References Cited

U.S. PATENT DOCUMENTS

| | | | | |
|---|---|---|---|---|
| 4,939,038 | A * | 7/1990 | Inabata | 428/402 |
| 5,195,969 | A | 3/1993 | Wang et al. | |
| 5,201,314 | A * | 4/1993 | Bosley et al. | 600/458 |
| 5,228,494 | A * | 7/1993 | Rohatgi | 164/97 |
| 5,270,086 | A | 12/1993 | Hamlin | |
| 5,366,504 | A | 11/1994 | Andersen et al. | |
| 5,439,627 | A * | 8/1995 | De Jager | 264/129 |
| 5,605,693 | A | 2/1997 | Seare, Jr. | |
| 5,629,077 | A | 5/1997 | Turnlund et al. | |
| 5,674,242 | A | 10/1997 | Phan et al. | |
| 5,780,807 | A | 7/1998 | Saunders | |
| 5,919,126 | A | 7/1999 | Armini | |
| 6,187,037 | B1 * | 2/2001 | Satz | 623/1.34 |
| 6,287,331 | B1 | 9/2001 | Heath | |
| 6,364,902 | B1 | 4/2002 | Dickenson et al. | |
| 6,509,088 | B2 * | 1/2003 | Baxter | 428/293.1 |
| 6,620,192 | B1 | 9/2003 | Jalisi | |
| 6,652,967 | B2 * | 11/2003 | Yadav et al. | 428/403 |
| 6,723,120 | B2 | 4/2004 | Yan | |
| 7,270,679 | B2 * | 9/2007 | Istephanous et al. | 623/17.11 |
| 2002/0144757 | A1 | 10/2002 | Craig et al. | |
| 2002/0167438 | A1 * | 11/2002 | Kamata et al. | 342/1 |
| 2003/0003220 | A1 | 1/2003 | Zhong et al. | |
| 2003/0018380 | A1 | 1/2003 | Craig et al. | |
| 2003/0059331 | A1 * | 3/2003 | Shinkai et al. | 419/5 |
| 2003/0060873 | A1 | 3/2003 | Gertner et al. | |
| 2003/0077200 | A1 | 4/2003 | Craig et al. | |
| 2003/0185895 | A1 | 10/2003 | Lanphere et al. | |

(Continued)

FOREIGN PATENT DOCUMENTS

WO   2004/108021 A2   12/2004

OTHER PUBLICATIONS

International Preliminary Report on Patentability mailed Oct. 18, 2007 in PCT/US2006/011458, 8 pages.

(Continued)

*Primary Examiner*—Monique R Jackson
(74) *Attorney, Agent, or Firm*—Fish & Richardson P.C.

(57) ABSTRACT

Medical devices, such as endoprostheses, and methods of making the devices are disclosed. In some embodiments, a medical device includes a composite having a metallic matrix and a plurality of particles in the matrix, the particles and the matrix having different compositions.

8 Claims, 3 Drawing Sheets

U.S. PATENT DOCUMENTS

| | | |
|---|---|---|
| 2004/0044397 A1 | 3/2004 | Stinson |
| 2004/0143317 A1 | 7/2004 | Stinson et al. |
| 2005/0059889 A1 | 3/2005 | Mayer |
| 2005/0070990 A1 | 3/2005 | Stinson |
| 2005/0131522 A1 | 6/2005 | Stinson et al. |
| 2005/0209680 A1 | 9/2005 | Gale et al. |
| 2005/0266040 A1* | 12/2005 | Gerberding .................. 424/423 |
| 2006/0065330 A1* | 3/2006 | Cooper et al. ............... 148/538 |
| 2006/0129215 A1* | 6/2006 | Helmus et al. .............. 607/115 |

OTHER PUBLICATIONS

R. Erikson, "Syntactic Metals: Flightweight Materials," *Advanced Materials & Processes*, vol. 160, No. 12, Dec. 2002, pp. 44-47.

U.S. Appl. No. 11/035,316, filed Jan. 13, 2005, Stinson et al.

Schetky, "Shape-Memory Alloys," *Encyclopedia of Chemical Technology*, Third Edition, vol. 20, John Wiley & Sons, New York, pp. 726-736 (1982).

* cited by examiner

MEDICAL DEVICES INCLUDING COMPOSITES

TECHNICAL FIELD

The invention relates to medical devices, such as endoprostheses (e.g., stents).

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly. Methods of monitoring a medical device include X-ray fluoroscopy, computed tomography (CT), and magnetic resonance imaging (MRI).

SUMMARY

The invention relates to medical devices, such as endoprostheses.

In one aspect, the invention features medical devices including composites, such as syntactic metals, and methods of making the medical devices. The composites including a matrix and a plurality of particles in the matrix. The particles and the matrix may have the same composition or different compositions.

In another aspect, the invention features a medical device including a composite including a metallic matrix and a plurality of particles in the matrix, the particles and the matrix having different chemical compositions.

In another aspect, the invention features a method of making a medical device including forming a composite having a metallic matrix and a plurality of particles in the matrix, and using the composite to form at least a portion of the medical device. The composite can be formed by addressing a matrix material and the particles with a laser. Forming the composite may include varying the concentration of the particles in the composite. Forming the composite may include a process selected from the group consisting of cold compaction, sintering, hot isostatic pressing, and extrusion. The particles and the matrix may have the same composition, and the particles define cavities. The particles and the matrix may have different compositions.

In another aspect, the invention features a medical device including a composition including a metallic matrix and a plurality of cavities in the matrix. The cavities can be defined by particles having the same composition as the composition of the matrix, and/or the cavities can be defined by particles having a composition different from the composition of the matrix.

Aspects of the invention may include embodiments having one or more of the following features. The particles are substantially spherical. The particles have a higher density than the matrix. The particles have a lower density than the matrix. The particles have an average particle size of from about 100 nanometers to about 10 micrometers. The particles are solid. The particles define cavities. The particles include a metal or an alloy. The particles include a ceramic. The particles have different sizes. The particles have substantially the same size. The particles are elongated fibers. The fibers are substantially oriented along a predetermined direction. The medical device further includes a coating on the particles, the coating having a chemical composition different than the chemical compositions of the matrix and the particles. The composite includes from about 5 to about 50 percent by volume of the particles. The particles include a material selected from the group consisting of titanium, tantalum, nickel, and stainless steel. The matrix includes a material selected from the group consisting of tantalum, an alloy comprising tantalum, niobium, an alloy comprising niobium, titanium, an alloy comprising iron, and an alloy comprising nickel and titanium. The medical device is an endoprosthesis, such as a stent. The medical device includes a body having multiple layers, at least one of the layers including the composite. The medical device includes a first portion including the composite with a first concentration of the particles, and a second portion including the composite with a second concentration of the particles different than the first concentration. The medical device include a plurality of composites having different compositions.

Embodiments may include one or more of the following advantages. A medical device including the composite may have one or more properties that can be tailored and tuned. For example, the radiopacity and/or density of the composite can be tailored to provide enhanced visibility under X-ray fluoroscopy or CT, while still having good biocompatibility and MRI compatibility. The mechanical properties, such as stiffness and strength, can likewise by tailored and tuned. Different sections of a medical device can include similar composites but have different properties (such as radiopacity, strength, and stiffness), for example, by varying the selections of materials in the composite and/or by varying the concentrations of the materials. The composite can be conveniently formable, for example, into tubing.

Other aspects, features, and advantages will be apparent from the description of the preferred embodiments thereof and from the claims.

DETAILED DESCRIPTION

Figure 1:
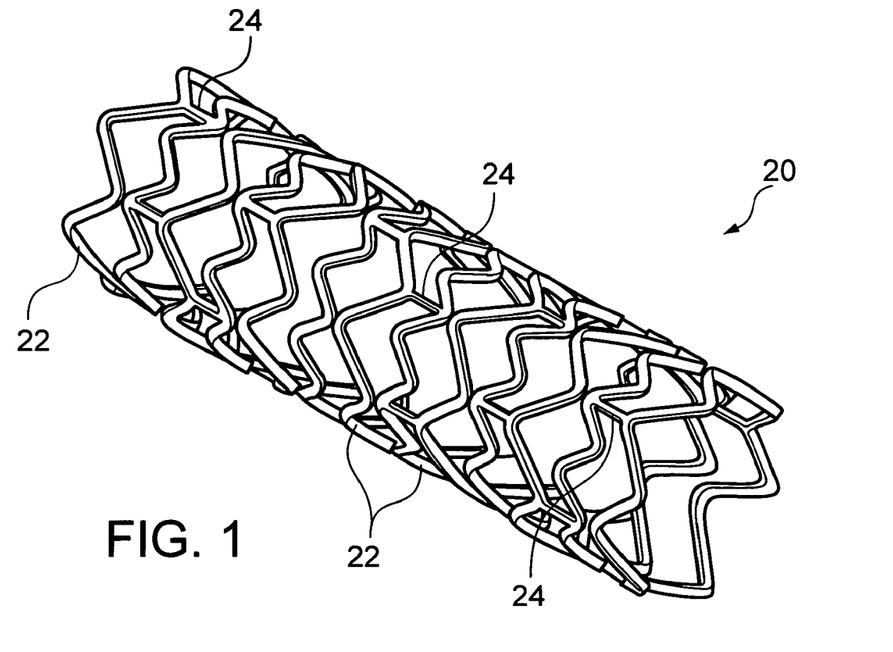
FIG. 1 is a perspective view of an embodiment of an expanded stent.

Referring to FIG. 1, a stent 20 has the form of a tubular member defined by a plurality of bands 22 and a plurality of connectors 24 that extend between and connect adjacent bands. During use, bands 22 are expanded from an initial, small diameter to a larger diameter to contact stent 20 against a wall of a vessel, thereby maintaining the patency of the vessel. Connectors 24 provide stent 20 with flexibility and conformability that allow the stent to adapt to the contours of the vessel.

Figure 2:
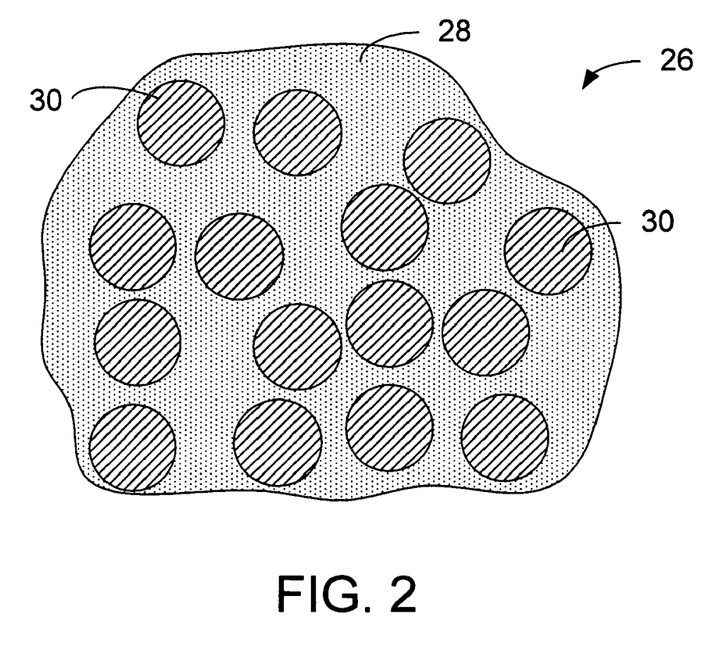
FIG. 2 is a detailed view of an embodiment of a composite.

Referring to FIG. 2, stent 20 includes a composite material 26 (sometimes called a syntactic metal) that has a metallic matrix 28 and a plurality of discrete particles 30 surrounded by and in the matrix. Composite material 26 is capable of providing stent 20 with tailored physical properties (such as density and radiopacity) and/or mechanical properties (such as strength). For example, a stent made of pure tantalum can have good biocompatibility and a low magnetic susceptibility that provides good visualization during magnetic resonance imaging (MRI). But in some embodiments, a pure tantalum stent may be too highly radiopaque, and as a result, visualization of the volume in the stent and of the tissue surrounding the stent during X-ray fluoroscopy or computed tomography (CT) may be obscured. To reduce the radiopacity, the stent can be made of a composite material including a tantalum matrix and particles of a less dense material, such as titanium. Since the titanium is less dense than tantalum, the radiopacity of a sample of the composite is reduced relative to an otherwise identical sample of tantalum. At the same time, since titanium also has good biocompatibility and a low magnetic susceptibility, the composite also has good biocompatibility and MRI compatibility. Other high density materials, such as molybdenum, niobium, platinum, and their alloys, can be similarly modified as described above for tantalum. Reducing the radiopacity may be particularly beneficial for thick walled stents (such as peripheral vascular stents). As another example, particles 30 can also be used to increase the radiopacity of metallic matrix 28, such as by incorporating tantalum particles in a titanium or titanium alloy matrix, or incorporating nickel or tantalum particles in a Nitinol matrix. Increasing the radiopacity may be particularly beneficial for thin walled stents and may obviate the need for radiopaque markers on stents in general.

Particles 30 can also enhance the mechanical properties of metallic matrix 28. Without wishing to be bound by theory, it is believed that particles 30 can increase the stiffness (tensile modulus) and/or strength (yield strength) of matrix 28 by dispersion strengthening. For example, particles of tantalum, tungsten, and/or rhenium can increase the stiffness of a matrix including titanium or niobium. The enhanced mechanical properties may allow the stent to be formed with reduced wall thickness without compromising the performance of the stent. A thinner walled stent may more easily delivered through a tortuous path, may be implanted in a smaller bodily vessel, and may allow more fluid flow through the stent.

Metallic matrix 28 can include (e.g., be manufactured from) one or more biocompatible materials with mechanical properties that allow a stent including composite material 26 to be compacted, and subsequently expanded to support a vessel. In some embodiments, stent 20 can have an ultimate tensile yield strength (YS) of about 20-150 ksi, greater than about 15% elongation to failure, and a modulus of elasticity of about 10-60 msi. When stent 20 is expanded, the material can be stretched to strains on the order of about 0.3. Examples of materials for metallic matrix 28 include stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. Ser. No. 10/672,891, filed Sep. 26, 2993, and entitled "Medical Devices and Methods of Making Same"; and U.S. Ser. No. 11/035,316, filed Jan. 3, 2005, and entitled "Medical Devices and Methods of Making Same". Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. Ser. No. 10/346,487, filed Jan. 17, 2003.

In some embodiments, metallic matrix 28 includes one or more materials that enhance visibility by MRI. Examples of MRI materials include non-ferrous metals (e.g., copper, silver, platinum, or gold) and non-ferrous metal-alloys containing paramagnetic elements (e.g., dysprosium or gadolinium) such as terbium-dysprosium, dysprosium, and gadolinium. Alternatively or additionally, metallic matrix 28 can include one or more materials having low magnetic susceptibility to reduce magnetic susceptibility artifacts, which during imaging can interfere with imaging of tissue, e.g., adjacent to and/or surrounding the stent. Low magnetic susceptibility materials include those described above, such as tantalum, platinum, titanium, niobium, copper, and alloys containing these elements.

Particles 30 can also include (e.g., be manufactured from) one or more biocompatible materials described above for matrix 28. The composition(s) of particles 30 can be different from the chemical composition(s) of matrix 28, and/or the particles and the matrix 28 can have the same composition(s). In embodiments in which the particles have the same composition(s) as the matrix, deleterious metallurgical phases, such as those that can form along the interface between the particles and matrix, may be prevented. For example, hollow particles, such as hollow tantalum spheres, can be incorporated within a tantalum matrix to lower the radiopacity of the tantalum matrix.

In embodiments in which particles 30 include one or more radiopaque materials to enhance radiopacity, the particles may include metallic elements having atomic numbers greater than 26 (e.g., greater than 43), and/or a density greater than about 9.9 g/cc. In certain embodiments, the radiopaque material is relatively absorptive of X-rays, e.g., having a linear attenuation coefficient of at least 25 $cm^{-1}$, e.g., at least 50 cm$^{-1}$, at 100 keV. Some radiopaque materials include tantalum, platinum, iridium, palladium, hafnium, tungsten, gold, ruthenium, and rhenium. The radiopaque material can include an alloy, such as a binary, a ternary or more complex alloy, containing one or more elements listed above with one or more other elements such as iron, nickel, cobalt, or titanium. Examples of alloys including one or more radiopaque materials are described in U.S. Application Publication US-2003-0018380-A1; US-2002-0144757-A1; and US-2003-0077200-A1.

Alternatively or additionally, particles 30 may include one or more materials to enhance MRI visibility. Example of MRI-visible materials include an oxide or a carbide layer of dysprosium or gadolinium (e.g., $Dy_2O_3$ or $Gd_2O_3$); a superparamagnetic material, such as $Fe_3O_4$, $CoFe_2O_4$, $MnFe_2O_4$, or $MgFe_2O_4$; and/or transition metal oxides (e.g., oxides of Fe, Co, Ni). Thus, the chemical composition of particles 30 need not be limited to metallic materials (e.g., metal and alloys), but the particles may include non-metallic compounds, such as ceramics, for example, oxides (e.g., aluminum oxide), carbides (e.g., silicon carbide), and nitrides (e.g., titanium nitrides), as further illustrated by the exemplary materials listed above.

The shape and size of particles 30 are not particularly limited. As shown in FIG. 2, particles 30 are generally spherical in shape to provide isotropic performance, but in other embodiments, non-spherical shapes, such as fibers, plates, chards, and prolated spheres, can also be used. For spherical particles, the diameters of the particles can range from about 10 nanometers to about 300 micrometers, such as, from about 100 nm to about 10 micrometers. For example, the diameters of spherical particles can be greater than or equal to about 100 nm, about 500 nm, about 1,000 nm, about 3,000 nm, about 5,000 nm, about 7,000 nm, or about 9,000 nm; and/or less than or equal to about 10,000 nm, about 9,000 nm, about 7,000 nm, about 5,000 nm, about 3,000 nm, about 1,000, or about 500 nm. For non-spherical particles, such as fibers, the largest dimension can also range from about 10 nanometers to about 500 micrometers, such as, from about 100 nm to about 100 micrometers. For example, the diameters of non-spherical particles can be greater than or equal to about 100 nm, about 500 nm, about 1,000 nm, about 3,000 nm, about 5,000 nm, about 7,000 nm, about 9,000 nm, about 10,000 nm, about 25,000 nm, about 50,000 nm, or about 75,000 nm; and/or less than or equal to about 100,000 nm, about 75,000 nm, about 50,000 nm, about 25,000 nm, about 10,000 nm, about 9,000 nm, about 7,000 nm, about 5,000 nm, about 3,000 nm, about 1,000, or about 500 nm.

In certain embodiments, such as when particles 30 are non-conductive (e.g., if they include a ceramic such as an oxide), the size of the particles are relatively small. As described below, in some methods of making a stent, electropolishing is used to finish the stent. When non-conductive particles are included in the composite material, electropolishing may preferentially remove the matrix material and not affect the non-conductive particles. As a result, pits may form at the surface of the stent if enough matrix material is removed to liberate the particles, or the surface may be rough with protruding non-conductive particles, both of which can cause the stent surface to be undesirably rough. By using small non-conductive particles, the size of any pits that are formed and the roughness caused by protruding non-conductive particles can be reduced. For example, the size of the particles can be selected to be equal to or smaller than the allowable peak or valley height, for example, to satisfy a predetermined surface roughness requirement (such as 3 microinches Ra). In some embodiments, the size of non-conductive particles is from about 80 nm to about 8 micrometers. For example, the size of the non-conductive particles can be greater than or equal to about 80 nm, about 500 nm, about 1,000 nm, about 2,000 nm, about 3,000 nm, about 4,000 nm, about 5,000 nm, about 6,000 nm, or about 7,000 nm; and/or less than or equal to about 8,000 nm, about 7,000 nm, about 6,000 nm, about 5,000 nm, about 4,000 nm, about 3,000 nm, about 2,000 nm, about 1,000 nm, or about 500 nm.

Non-spherical particles can be randomly distributed within a matrix or preferentially oriented in a predetermined direction within the matrix to provide anisotropic performance. For example, fibers that are oriented circumferentially around the tubular member can enhance the hoop strength of the tubular member, which helps stent 20 to resist compression, thereby maintaining the body vessel open. Fibers that are oriented radially can enhance the radial strength of the stent, and fibers that oriented longitudinally, i.e., parallel to the length of the stent can enhance axial stiffness. Magnetic non-spherical particles can be aligned by applying a magnetic field along a predetermined direction. Fibers can be formed having a first end heavier than a second end, e.g., by forming a stub on the first end or by tapering the size of the fiber. The fibers can then be placed into an unsolidified sheet of matrix material, in which the heavier ends of the fibers tend to align the fibers perpendicular to the longitudinal axis of the sheet. In other embodiments, asymmetrical fibers, e.g., those having one end heavier than another end, can be mixed with the matrix material and spin casted (e.g., about the longitudinal axis) in a mold to form a tubular member. The centrifugal force generated during spin casting can orient the fibers in the matrix material, e.g., the fibers can orient radially, with the heavier ends outward of the lighter ends. Other methods of aligning fibers and making stents with aligned fibers are disclosed in published patent application 2004-0044397. Within a composite material, particles 30 can have one or more shapes (e.g., spheres and fibers) and/or one or more sizes (e.g., a distribution of sizes).

Figure 3:
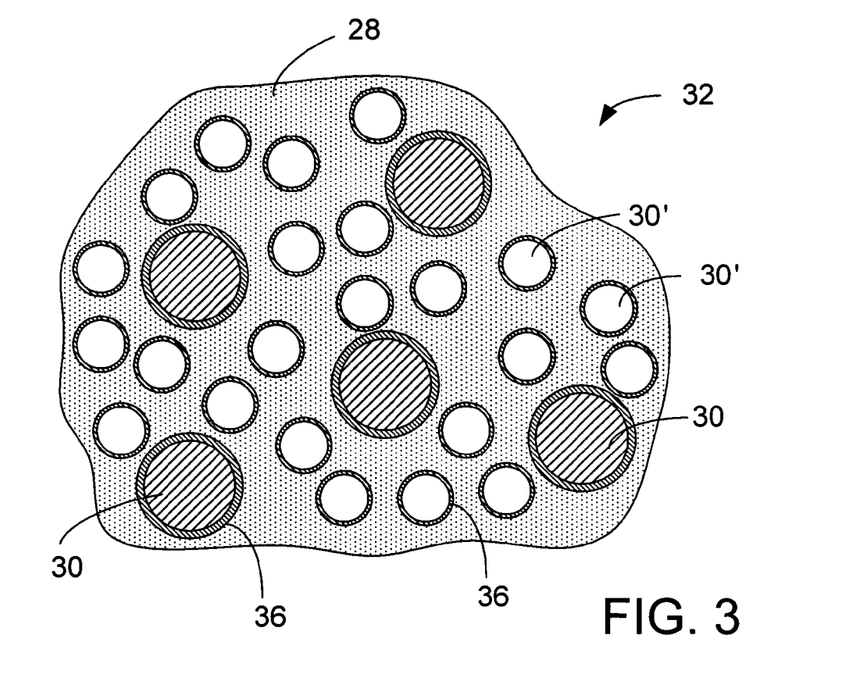
FIG. 3 is a detailed view of an embodiment of a composite.

Particles 30 can be solid (as shown in FIG. 2) or hollow. Referring to FIG. 3, a composite 32 includes metallic matrix 28, solid particles 30, and hollow particles 30' that define cavities 36. Hollow particles 30' can further decrease the density of composite 32, while still providing, for example, strengthening effects. Cavities 36 can have an average diameter or width from about 80 nm to about 9 micrometers. For example, the average diameter or width can be greater than or equal to about 80 nm, about 500 nm, about 1,000 nm, about 2,000 nm, about 3,000 nm, about 4,000 nm, about 5,000 nm, about 6,000 nm, about 7,000 nm, or about 8,000 nm; and/or less than or equal to about 9,000 nm, about 8,000 nm, about 7,000 nm, about 6,000 nm, about 5,000 nm, about 4,000 nm, about 3,000 nm, about 2,000 nm, about 1,000 nm, or about 500 nm. Hollow particles 32 with different size cavities or the same size cavities can be used. Hollow particles 32 can be made, for example, by using a puffing nozzle to blow bubbles from a flowing molten sheet of material, by using a concentric nozzle and a drop tower, by sol-gel methods, or by using precursor methods in which the sphere is formed within or around another material that is subsequently removed. Solid particles 30 can be made by powder atomization. Other methods of making particles include bubbling of molten material, sol-gel techniques, and precursor casting. As shown in FIG. 3, hollow particles 30' are smaller than solid particles 30, but in other embodiments, the hollow particles can be larger than the solid particles, particles 30', 30 can be of similar size, or a combination of sizes of particles can be used. Within a composite material, the particles can be all solid, all hollow, or as shown, a combination of hollow and solid particles.

Still referring to FIG. 3, in some embodiments, particles 30 include a coating 36 having a different chemical composition that the chemical composition of the particles and the matrix. Certain coatings 36 can be more compatible (e.g., miscible) with the matrix material and enhance incorporation of the particles into the matrix. Coating 36 may act as a buffer layer or a protective layer between the particles and the matrix by including a material that combines well (e.g., alloys well) the matrix material, for example, to reduce the formation of deleterious phases. For example, the radiopacity of titanium can be increased by sputter coating tungsten spheres with tantalum because tungsten and titanium can form undesirable intermetallic phases, such as omega.

The total concentration of particles in metallic matrix 28 can also vary. In some embodiments, a composite material includes from about 1 to about 80 volume percent of particles, such as from about 5 to about 50 volume percent of particles. The volume percent of particles can be greater than or equal to about 1%, about 5%, about 10%, about 20%, about 30%, about 40%, about 50%, about 60%, or about 70%; and/or less than or equal to about 80%, about 70%, about 60%, about 50%, about 40%, about 30%, about 20%, about 10%, or about 5%. Multiple composite materials with different concentrations of particles, and/or different compositions of particles and/or matrix can be used in a medical device. For example, for a stent having a composite material including a stainless steel matrix and tantalum particles, the end portions of the stent may have a higher concentration of tantalum than other portions of the stent to enhance contrast and visualization of the stent during fluoroscopy. As another example, the concentration of particles at the end portions can be selected to make the end portions more flexible so that the end portions can flare out and secure the stent against a vessel. The concentration of particles at the middle portion can be selected to have a relatively low yield strength so that the stent can be easily plastically deformed with little recoil during expansion of the stent.

The selections of materials for metallic matrix 28 and the particles in the matrix are guided by the desired properties of the composite material. For example, as discussed above, the radiopacity of matrix 28 can be increased or decreased by incorporating denser or less dense particles, respectively. Particles of one or more chemical compositions, sizes, type (e.g., solid or hollow), and/or shape can be used to tailor and tune the desired properties. Other considerations for the selection of materials include the compatibility between the materials. For example, the materials for matrix 28 and the particles may be selected to be miscible and not to form undesirable metallurgical phases that are deleterious to engineering properties. The materials for matrix 28 and the particles may be selected so that their reduction potentials are relatively similar to reduce the occurrence of galvanic corrosion in the body. The melting points of the materials for matrix 28 and the particles may also be different (e.g., different by greater than about 50° C.) so that the particles do not melt if the matrix material is molten during fabrication of the composite material. In some embodiments, the melting points of the materials for matrix 28 and the particles may be somewhat compatible so that during fabrication (e.g., laser cutting described below) the composite material does not segregate, or one material does not substantially preferential melt over another material. Particles 30 may be selected to have ductility similar to the matrix or at least high enough to deform during cold working of the matrix (e.g., during tube manufacturing) without fracturing. For example, titanium particles that have been annealed (softened) after quench atomization may be more likely to deform within a tantalum matrix than as-quenched particles.

Figure 4:
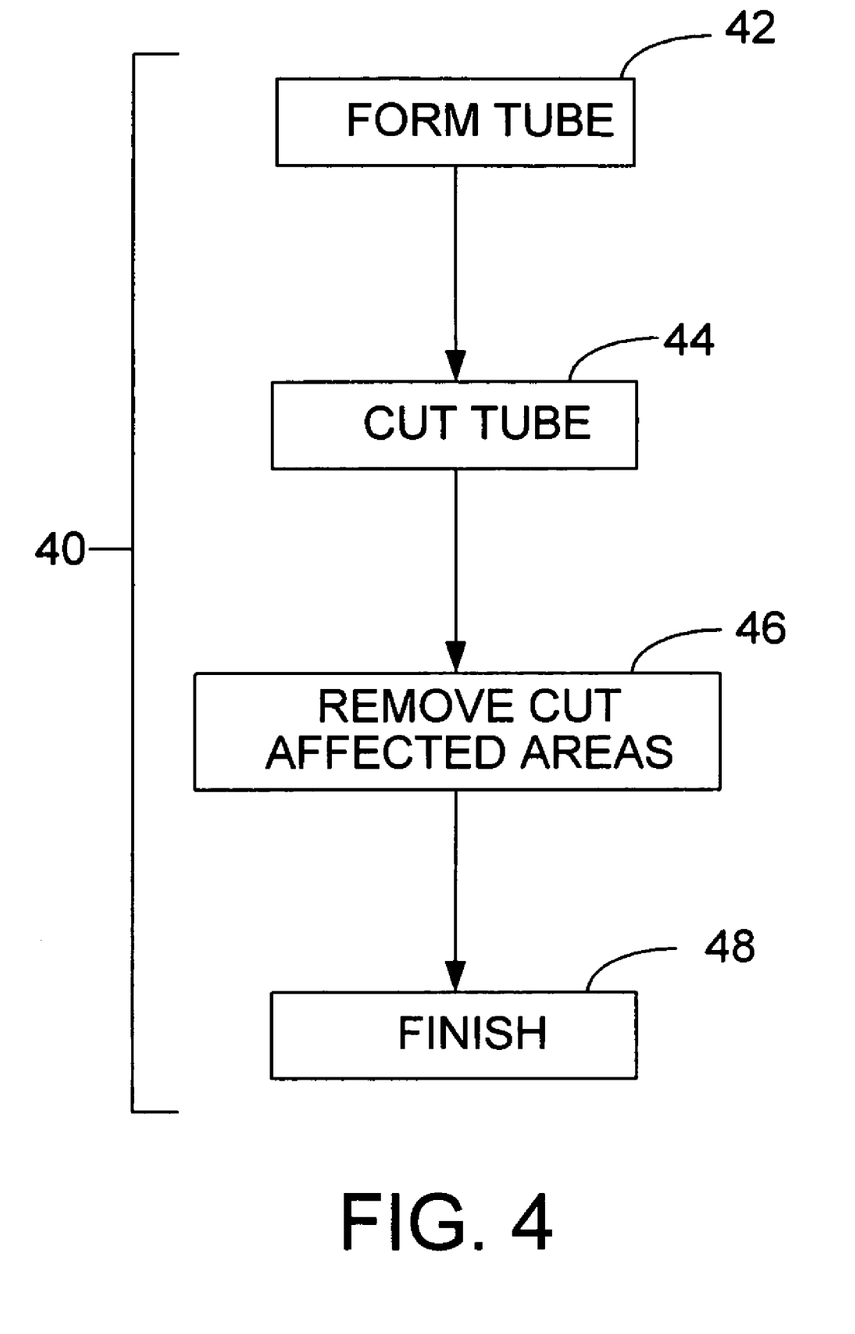
FIG. 4 is a flow chart of an embodiment of a method of making a stent.

FIG. 4 shows a method 40 of making stent 20. As shown, method 40 includes forming a tube (step 42) including composite material 26 that makes up the tubular member of stent 20. The tube is subsequently cut to form bands 22 and connectors 24 (step 44) to produce an unfinished stent. Areas of the unfinished stent affected by the cutting may be subsequently removed (step 46). The unfinished stent may be finished to form stent 20 (step 48).

Figure 5:
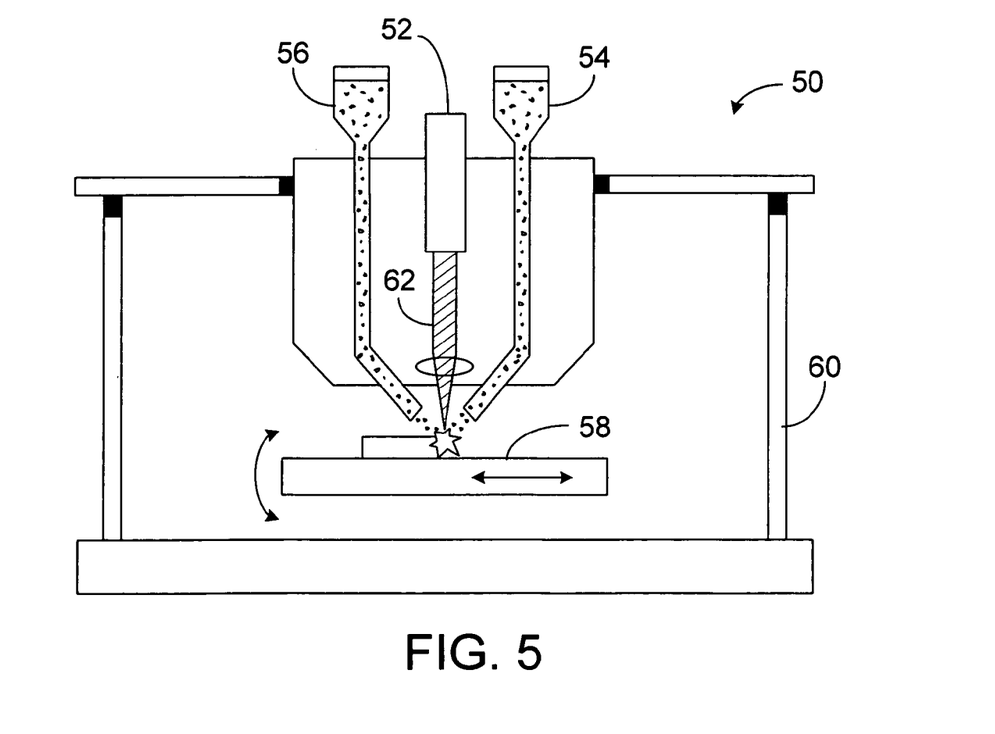
FIG. 5 is a diagrammatic view of a system for making a medical device.

The tube that makes up the tubular member of stent 20 can be formed using metallurgical techniques, such as laser forming (step 32). Referring to FIG. 5, a system 50 for making the tubular member is shown. System 50 includes a laser 52, a first hopper 54 containing a material for metallic matrix 28, a second hopper 56 containing a material for particles 30, a movable cylindrical substrate 58, and a chamber 60. Hoppers 54, 56 are configured to selectively deliver their respective materials onto substrate 58. Laser 52 is configured to deliver an energy beam 62 to where the materials from hoppers 54, 56 are delivered on substrate 58. Substrate 58, which is made from a removable material such as carbon steel, cadmium, lead, magnesium, tin, and zinc, can be translated and rotated to vary the position on the substrate where the materials are deposited and energy beam 62 is addressed. Chamber 60 can be filled and purged with an inert gas to prevent oxidation or contamination of the materials. During fabrication, hoppers 54, 56 deliver their respective material onto substrate 58, and at the same time, laser 52 delivers sufficient energy to melt the matrix material to encapsulate the particles, thereby forming the composite material. To vary the concentrations of the matrix material and/or the particles material, the delivery rate(s) of the hopper(s) can be varied. To vary the compositions or types of particles or matrix materials, additional hoppers containing the desired materials can be used. Substrate 58 is concurrently translated and/or rotated to form a tubular member made of the composite material. In some embodiments, multiple layers of composite material are deposited to form the resulting tubular structure. After the tubular member is made, substrate 58 can be removed by dissolution (e.g., by immersion in an acid such as nitric acid), by mechanical removal (e.g., by grinding), by melting (e.g., for substrate materials having sufficiently low melting points), and/or subliming. Laser forming is described in commonly assigned U.S. Ser. No. 10/732,492, filed on Dec. 10, 2003, and entitled "Medical Devices and Methods of Making the Same", hereby incorporated by reference.

Alternatively or additionally, other thermomechanical processes can also be used to form a tubular member made of a mechanical composite material. For example, the matrix material need not be molten to form the composite material. The matrix material and the particles can be combined by powder metallurgy techniques (such as pressure casting, sintering, hot isostatic pressing, and hot working), slurry mixing, direct laser sintering, and vacuum plasma deposition, to form a raw material that is subsequently shaped into a feedstock, such as a hollow tubular member. A medical device including a composite material having variable concentrations of particles can be made by joining multiple portions (e.g., billets) of different particle concentrations by sintering. Stents with layers of composite material of different particle concentrations can be formed by sequentially adding the selected composite materials into a mold to form the tubular member.

In some embodiments, the hollow tubular member including the composite material can be drawn through a series of dies with progressively smaller circular openings to plastically deform the member to a targeted size and shape. The plastic deformation strain can harden the member (and increases its yield strength) and elongate the grains along the longitudinal axis of the member. The deformed member can be heat treated (e.g., annealed above the recrystallization temperature and/or hot isostatically pressed) to transform the elongated grain structure into an initial grain structure, e.g., one including equiaxed grains. Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed, as shown, by cutting the tube (step 44). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed (step 46). For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after step 46 is performed. "Near-net size" means that the tube has a relatively thin envelope of material that is removed to provide a finished stent. In some embodiments, the tube is formed less than about 25% oversized, e.g., less than about 15%, 10%, or 5% oversized.

The unfinished stent is then finished to form stent 20. The unfinished stent can be finished, for example, by electropolishing to a smooth finish. Since the unfinished stent can be formed to near-net size, relatively little of the unfinished stent need to be removed to finish the stent. As a result, further processing (which can damage the stent) and costly materials can be reduced. In some embodiments, about 0.0001 inch of the stent material can be removed by chemical milling and/or electropolishing to yield a stent.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

As an example, while stent 20 is shown above as being formed wholly of composite material 26, in other embodiments, the composite material forms one or more selected portions of the medical device. For example, stent 20 can include multiple layers in which one or more layers include a composite material, and one or more layers do not include a composite material. The layer(s) that includes a composite material can include the same composite material or different composite materials. The layer(s) that does not include a composite material may include one or more of the biocompatible matrix materials listed above. The layering of the composite material provides yet another way to tailor and tune the properties of the medical device. Stents including multiple layers are described, for example, in published patent application 2004-0044397, and Heath, U.S. Pat. No. 6,287,331.

Stent 20 can be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

In some embodiments, stent 20 can be formed by fabricating a wire including the composite material, and knitting and/or weaving the wire into a tubular member. The composite materials described herein can be used to form other medical devices. For example, the composite materials can be used to form a guidewire or a hypotube. A guidewire may have portions including different concentrations of particles to provide a flexible distal section for good trackability and a stiff proximal section for good pushability. The composite material can be used to form medical implants, such as hip stems and knee trays. The composite material can be used to form metal staples and wires used for wound closure so that they can be compatible with imaging techniques.

The following examples are illustrative and not intended to be limiting.

EXAMPLE 1

Titanium-6 aluminum-4 vanadium (Ti-6A1-4V) alloy powder in the size range of 50-500 microns can be mechanically blended with 40 volume percent of solid tantalum particles in the size range of 500 nanometers to 5 microns. The mixture can be transferred into a titanium or steel cylindrical can mold that has external dimensions of 3 inches diameter and 20 inches long. The can may be sealed and evacuated with a vacuum pumping system. The evacuated can may be then hot isostatically pressed (HIP) at 2150F/25 ksi/24 hours.

After the HIP operation, the can may be machined (if titanium) or dissolved (if steel) away to leave a billet of a composite.

The composite billet can be machined to a uniform diameter with end faces perpendicular to the long axis of the cylinder. The machined billet can be hot extruded at 2000F to a 1.5" diameter rod. The rod can be machined, straightened, and cut to produce finished rods that are 1.0" diameter and 15" long. The finished rods can be annealed at 1700F in a vacuum furnace for one hour and cooled in argon gas. The heat treated rods can then be gun drilled and subjected to repeated cold draw and anneal operations to form stent tubings with a 0.08" OD and 0.004" wall thickness.

A stent tubing can be subjected to laser machining to create a strut pattern of a stent. The laser cut stent can be subjected to chemical milling and electropolishing to produce a finished stent. The stent may have low magnetic susceptibility because it does not include any ferromagnetic elements, and as a result, may have lower magnetic susceptibility artifact in MRI than, for example, a 316L stainless steel stent. The composite stent may have higher radiopacity than Ti-6A1-4V, and as a result, may be more visible in radiography than a titanium stent. The composite stent may have a higher modulus than a Ti-6A1-4V stent, because of the strengthening and stiffening from the tantalum particles, and as a result, may have less elastic recoil during crimping and expansion than a titanium stent.

EXAMPLE 2

50 tantalum-50 niobium (Ta-50Nb) alloy powder in the size range of 50-500 microns can be mechanically blended with 50 volume percent of solid commercially pure grade 4 titanium particles in the size range of 500 nanometers to 5 microns. The mixture can be transferred into a titanium or steel cylindrical can mold that has external dimensions of 3 inches diameter and 20 inches long. The can may be sealed and evacuated with a vacuum pumping system. The evacuated can may then be hot isostatically pressed (HIP) at 2150F/25 ksi/24 hours. After the HIP operation, the can may be machined (if titanium) or dissolved (if steel) away to leave a billet of a composite. The billet may also be produced with hollow titanium spheres by the same process or by the SynFoam™ process (and procured from Powdermet, Inc.).

The composite or SynFoam™ billet may machined to a uniform diameter with end faces perpendicular to the long axis of the cylinder. The machined billet may be hot extruded at 2300F to a 1.5" diameter rod. The rod may be machined, straightened, and cut to produce finished rods that are 1.0" diameter and 15" long. The finished rods may be annealed at 2300F in a vacuum furnace for one hour and cooled in argon gas. The heat treated rods may then be gun drilled and subjected to repeated cold draw and anneal operations to form stent tubings with a 0.08" OD and 0.004" wall thickness.

A stent tubing may be subjected to laser machining to create a stent strut pattern. The laser cut stent can be subjected to chemical milling and electropolishing to produce a finished stent. The stent may have low magnetic susceptibility because it is not composed of any ferromagnetic elements, and as a result, can have lower magnetic susceptibility artifact in MRI than, for example, a 316L stainless steel stent. The composite stent can have lower density and radiopacity than tantalum or Ta-50Nb, and as a result, can have less attenuation ("blooming") artifact in radiography than a Ta or Ta-50Nb stent. The composite stent can have a higher modulus than a Ta-50Nb stent, because of the strengthening and stiffening from the particles, and as a result, can have less elastic recoil during crimping and expansion than a titanium stent.

All publications, references, applications, and patents referred to herein are incorporated by reference in their entirety.

Other embodiments are within the claims.

What is claimed is:

1. A medical device, comprising a composite comprising a metallic matrix and a plurality of particles in the matrix, the matrix comprising a material selected from the group consisting of titanium, an alloy comprising iron, and an alloy comprising nickel and titanium, the particles comprising a material selected from the group consisting of platinum and nickel, the particles having a higher density than the matrix, the particles having an average particle size of from about 100 nanometers to about 10 micrometers, wherein the medical device is an endoprosthesis.

2. The medical device of claim 1, wherein the particles are substantially spherical.

3. The medical device of claim 1, wherein the particles are solid.

4. The medical device of claim 1, wherein the metallic matrix comprises an alloy comprising nickel and titanium and wherein the particles comprise nickel.

5. The medical device of claim 1, wherein the metallic matrix comprises an alloy comprising iron and wherein the particles comprise platinum.

6. The medical device of claim 1, further comprising a coating on the particles, the coating having a chemical composition different than the chemical compositions of the matrix and the particles.

7. The medical device of claim 1, wherein the composite comprises from about 5 to about 50 percent by volume of the particles.

8. The medical device of claim 1, wherein the medical device is a stent.

* * * * *

UNITED STATES PATENT AND TRADEMARK OFFICE
CERTIFICATE OF CORRECTION

PATENT NO. : 7,641,983 B2
APPLICATION NO. : 11/098201
DATED : January 5, 2010
INVENTOR(S) : Jonathan S. Stinson Page 1 of 1

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 659 days.

should read (*) Notice: Subject to any disclaimer, the term of this patent is extended or adjusted under 35 U.S.C. 154(b) by 1,300 days.

Column 12, line 24 (Claim 1), before "matrix" please insert --metallic--.

Signed and Sealed this

Twenty-second Day of June, 2010

David J. Kappos
*Director of the United States Patent and Trademark Office*